United States Patent [19]

Neely

[11] 4,267,055
[45] May 12, 1981

[54] SEPARATION OF MORE PLANAR MOLECULES FROM LESS PLANAR MOLECULES

[75] Inventor: James W. Neely, North Wales, Pa.

[73] Assignee: Rohm and Haas Company, Philadelphia, Pa.

[21] Appl. No.: 71,808

[22] Filed: Sep. 4, 1979

[51] Int. Cl.³ .............................................. B01D 15/00
[52] U.S. Cl. .................................... 210/670; 210/690; 560/218; 562/472; 562/600; 585/828; 585/830
[58] Field of Search ................... 55/74; 210/30 R, 39, 210/40; 560/218; 562/472, 600; 585/820, 826, 827, 830, 828, 831

[56] References Cited

U.S. PATENT DOCUMENTS

| | | | |
|---|---|---|---|
| 3,066,099 | 11/1962 | Mohun | 252/444 |
| 3,222,412 | 12/1965 | Mason et al. | 585/830 |
| 3,632,626 | 1/1972 | Schneller et al. | 560/218 |
| 4,040,990 | 8/1977 | Neely | 521/29 |

Primary Examiner—Ivars C. Cintins
Attorney, Agent, or Firm—John E. Taylor, III

[57] ABSTRACT

Planar organic molecules, such as divinylbenzene or para-dioxin molecules, are adsorbed from mixtures of planar and non-planar molecules, such as commercial divinylbenzenes containing non-planar ethylvinylbenzene, or commercial 2,4,5-T herbicide containing non-planar 2,4,5-trichlorophenoxyacetic acid, by partially pyrolyzed, macroporous, resinous polymer particles.

10 Claims, No Drawings

SEPARATION OF MORE PLANAR MOLECULES FROM LESS PLANAR MOLECULES

This application concerns the separation of highly planar molecules from less planar molecules. In particular, it concerns the use of partially pyrolyzed beads of macroporous resinous polymer to separate such molecules.

Molecular sieves provide a well-known means of separating components of mixtures based on the dimensions of the component molecules. Such separations are frequently used to separate mixtures of compounds with boiling points too similar for practical fractional distillation, and are illustrated by Allen, U.S. Pat. No. 3,960,520; Rosback, U.S. Pat. No. 3,960,774; Kanaoka et al., U.S. Pat. No. 4,069,172; and Rosback et al., U.S. Pat. No. 4,079,094. These separation processes depend upon the pore sizes of crystalline aluminosilicates, or zeolites. Such materials possess round, or cylindrical, apertures which may be controlled during the manufacturing process to uniform dimensions. The typical range of apertures within which zeolite molecular sieves may be produced is from about 3 to about 20 Å units (0.3—2.0 nanometers), and a given molecular sieve material typically possesses a very narrow aperture size distribution within that range. Typical materials separated by such molecular sieves include fixed gases such as nitrogen, oxygen and carbon dioxide (3.3 Å), aliphatic hydrocarbons such as n-butane (4.3 Å), isobutane (5.0 Å), neopentane (6.2 Å), and cyclic compounds including alicyclic molecules such as cyclohexane (4.8 Å thick, 6.8 Å wide) and aromatic ones such as benzene (3.7 Å thick, 7.0 Å wide) and the xylene isomers. In most of these separations, molecules smaller than the apertures penetrate the zeolite lattice and are trapped, or adsorbed, while larger molecules pass the zeolite material unaffected. The adsorbed molecules may be desorbed later by a material for which the zeolite has a stronger affinity than for the adsorbed molecule.

Carbonized adsorbents are widely used for separation, and such materials as charcoals and mineral coals have been shown to possess molecular sieve properties. Mohun, U.S. Pat. No. 3,066,099, discusses the structure and activity of these materials. Mason et al., U.S. Pat. No. 3,222,412, teaches the oxidation of anthracite to produce an adsorbent that adsorbs planar molecules but rejects molecules of 3-dimensional configuration. Thus, cyclohexane may be separated from benzene using this material. Oxidized anthracities, like other carbonized materials showing molecular sieve activity, suffer particularly from the disadvantages of particle friability and lack of control over the starting material.

My U.S. Pat. No. 4,040,990, which is hereby incorporated into this specification by reference, discloses partially pyrolyzed particles or macroporous, synthetic polymers. These particles have a high resistance to crushing and particle sloughage, and because the starting materials are synthetic polymers, they may be carefully controlled to produce final products with highly consistent properties. These particles are known to have general adsorbent properties.

It has now been discovered that certain of these partially pyrolyzed, macroporous polymer particles of U.S. Pat. No. 4,040,990, and their analogs pyrolyzed at higher temperatures, as for example the particles of British Pat. No. 1,525,420, selectively and reversibly adsorb planar molecules in preference to less planar molecules. Mixtures of planar and non-planar molecules may be contacted with these particles to adsorb the planar molecules, and the particles may subsequently be separated from the mixture to reduce the concentration of planar molecules in the mixture. The particles may be further treated to elute the adsorbed, planar molecules, in many cases essentially free of the non-planar molecules from the mixture. The separation process may involve contacting a quantity of such a mixture with the particles and allowing them to remain in contact until an equilibrium condition is approached, followed by separating the mixture from the particles, or it may involve passing a continuous stream of the mixture through a bed of the particles. These methods of contacting a solid adsorbent and a fluid mixture, and their several modifications, are well known in the ion exchange and adsorbent arts.

Planar molecules which may be selectively and reversibly adsorbed by the partially pyrolyzed, macroporous polymer particles include polynuclear aromatic and substituted polynuclear aromatic compounds such as, for example, napthalene, indene, anthracene, phenanthrene, benzonapthene, acenaphthanthracene, 1,2-benzanthracene, benzanthrene, 1,9-benzanthr-10-one, 10,11-benzofluoranthrene, 3,4-benzopyrene, and 6,12-chrysoquinone; mononuclear, substituted aromatic compounds with non-bulky substituents, such as, for example, benzene, toluene, xylenes, styrene, divinylbenzenes, phenols, halogenated phenols, quinones, hydroquinones, acridine, and 9,10-anthraquinone; and such heterocyclic aromatic, condensed heterocyclic aromatic and substituted, condensed, heterocyclic aromatic compounds as isoquinoline, $\beta$-anthraquinoline, dibenzo-p-dioxins, halogenated dibenzo-p-dioxins, azobenzene, halogenated azobenzenes, tetrahydrofuran, 1,3,5-triazene, and xanthopterin.

Examples of useful processes which may employ the method of this invention include the removal of polymerization inhibitors from monomers, e.g., removing hydroquinone from methyl methacrylate; the removal of toxic, polynuclear aromtic compounds from coke oven waste streams; the removal of the highly toxic dioxins from the herbicide 2,4,5-trichlorophenoxyacetic acid (2,4,5-T); and the removal of the diethylenic cross-linking monomer, divinylbenzene, from the non-cross-linking, monoethylenic monomer, ethylvinylbenzene, which occurs as a major contaminant of commercial divinylbenzene.

The preferred particles of partially pyrolyzed, macroporous polymer for use in the practice of this invention are those pyrolyzed at a temperature of at least 500° C., and more preferably between about 800° and about 1200° C. The remaining parameters for these particles, including monomers from which the polymers are prepared, carbon-fixing moieties, and the like, are as taught in the above-referenced U.S. Pat. No. 4,040,990. A preferred source of the carbon-fixing moiety is sulfuric acid, which may be imbibed into the pores of the polymer prior to pyrolysis, so that sulfonation of the polymer occurs during the initial heating, and pyrolysis of the resulting sulfonate-functionalized polymer occurs as the temperature is increased.

The following specific process for the separation of planar divinylbenzenes from non-planar ethylvinylbenzene is typical of the useful separations which may employ the process of the present invention. A commercial mixture of ethylvinylbenzene and divinylbenzenes is contacted with the partially pyrolyzed, macroporous polymer particles, the particles are separated from the mixture after having adsorbed divinylbenzenes, and the particles are subsequently washed free of the mixture with a non-eluting solvent such as methanol or hexane. The divinylbenzenes, essentially free of ethylvinylbenzene, are then eluted from the adsorbent particles with an eluting solvent such as toluene.

The highly toxic, planar dioxins, such as 2,3,7,8-tetrachlorodibenzo-p-dioxin(TCDD), may be separated from 2,4,5-trichlorophenoxyacetic acid (2,4,5-T), in which they occur as a by-product. A solution of 2,4,5-T is contacted with the partially pyrolyzed, macroporous polymer particles, and the particles are separated from the solution after having adsorbed dioxins. The particles may then be washed with a non-eluting solvent to recover 2,4,5-T. Because it is desirable to reduce the movement of a toxic material through the environment, the adsorbed dioxins may be left fixed in the adsorbent particles for disposal, as by burial or burning, rather than being eluted and handled for disposal in solution form.

The following examples are intended to more specifically illustrate, but not to limit, the process of the present invention. All percentages are by weight unless otherwise indicated, and all reagents used are good commercial quality unless otherwise indicated.

In the following examples the adsorbents are prepared according to the above-referenced U.S. Pat. No. 4,040,990 from sulfonated, macroporous resin beads of styrene-20% divinylbenzene. Adsorbent A is partially pyrolyzed at 800° C. in a nitrogen atmosphere, while Adsorbent B is Adsorbent A subsequently exposed to oxygen at 500° C. for a brief period. Adsorbent C is partially pyrolyzed at 500° C. in a nitrogen atmosphere.

EXAMPLE 1

This example illustrates the use of Adsorbent B for the chromatographic separation of pure divinylbenzenes from ethylvinylbenzene in the mixtures that are commercial divinylbenzene.

A 33.57-g sample of Adsorbent B with particle size smaller than 60 mesh was suspended in hexane and transferred to a column having a diameter of 1 cm. The resulting bed volume was 55 ml. A 2.382-g sample of commercial divinylbenzene containing 1.077 g ethylvinylbenzene (EVB), 1.003 g m-divinylbenzene (m-DVB) and 0.302 g p-divinylbenzen (p-DVB) was transferred to the top of the column. The sample was washed through the column with 4 bed volumes of hexane, to elute the ethylvinylbenzene, followed by 4 bed volumes of toluene, to elute the divinylbenzenes, at the same flow rate of 3 bed volumes per hour. Fractional cuts of the eluate were taken after passage of the indicated number of bed volumes of solvent, and were analyzed for ethylvinylbenzene, m-divinylbenzene and p-divinylbenzene. The results are shown below in Table I (the percent value greater than 100% for m-DVB is an analytical artifact).

TABLE I

| Eluting Solvent | Bed Volumes of Solvent | Cumulative Wt % | | |
|---|---|---|---|---|
| | | EVB | m-DVB | p-DVB |
| Hexane | 0.5 | 0 | 0 | 0 |
| | 1.0 | 6.9 | 0 | 0 |
| | 1.5 | 38.0 | 0 | 0 |
| | 2.0 | 39.3 | 2.3 | 0 |
| | 2.5 | 59.2 | 2.3 | 0 |
| | 3.0 | 72.1 | 2.3 | 0 |
| | 3.5 | 79.6 | 2.3 | 0 |
| | 4.0 | 83.1 | 3.1 | 0 |
| Toluene | 0.50 | 86.5 | 4.9 | 0 |
| | 0.75 | 90.7 | 42.0 | 0 |
| | 1.00 | 91.9 | 80.8 | 40.3 |
| | 1.25 | 92.8 | 92.5 | 64.6 |
| | 1.50 | 93.2 | 97.4 | 77.2 |
| | 1.75 | 93.4 | 99.9 | 84.0 |
| | 2.00 | 93.4 | 101.5 | 88.5 |
| | 2.25 | 93.4 | 102.5 | 90.4 |
| | 2.50 | 93.4 | 103.3 | 92.6 |
| | 4.00 | 93.4 | 105.3 | 96.2 |

EXAMPLE 2

This example illustrates the use of styrene as an eluent for divinylbenzene in the chromatographic separation described in Example 1.

A column was prepared as described in Example 1, using 16.8 g of Adsorbent B, with particle sizes smaller than 60 mesh, in a 1 cm. diameter column, producing a bed volume of 27 ml. A 1.196-g sample of commercial divinylbenzene containing 0.511 g ethylvinylbenzene, 0.457 g m-divinylbenzene and 0.228 g p-divinylbenzene was charged to the column followed by a hexane wash of 3 bed volumes. The divinylbenzenes were eluted from the column with 1.67 bed volumes of styrene. The results are given below in Table II.

TABLE II

| Eluting Solvent | Bed Volumes of Solvent | Component Wt. (g) | | | | | Cumulative Wt. % | | |
|---|---|---|---|---|---|---|---|---|---|
| | | EVB | m-DVB | p-DVB | Hexane | Styrene | EVB | m-DVB | p-DVB |
| Hexane | 1–3 | 0.39 | 0.026 | 0 | 52.9 | 0 | 76.3 | 5.8 | 0 |
| Styrene | 1/6 | 0.008 | 0.0035 | 0 | 3.05 | 0 | 77.9 | 6.5 | 0 |
| | 1/3 | 0.0229 | 0.022 | 0.00 | 2.89 | 0.07 | 82.4 | 11.3 | 0.02 |
| | 1/2 | 0.032 | 0.217 | 0.100 | 1.15 | 3.35 | 88.6 | 58.7 | 42.3 |
| | 2/3 | 0.012 | 0.067 | 0.053 | 0.153 | 4.79 | 90.9 | 73.2 | 65.7 |
| | 5/6 | 0.006 | 0.021 | 0.019 | .0621 | 5.15 | 92.0 | 77.8 | 74.2 |
| | 1 | 0.004 | 0.009 | 0.006 | 0.164 | 4.92 | 92.7 | 79.8 | 76.8 |
| | 1 1/6 | 0.002 | 0.005 | 0.003 | 0.029 | 5.06 | 93.1 | 80.8 | 78.0 |
| | 1 1/3 | 0.002 | 0.003 | 0.002 | 0.021 | 5.10 | 93.6 | 81.5 | 78.8 |
| | 1 1/2 | 0.001 | 0.002 | 0.001 | 0.007 | 5.14 | 93.8 | 82.0 | 79.4 |
| | 1 2/3 | 0 | 0.002 | 0.0007 | 0 | 5.33 | 93.8 | 82.4 | 79.7 |

EXAMPLE 3

This example illustrates a batchwise separation of divinylbenzene from the commercial mixture of divinylbenzene.

A 10-ml sample of Adsorbent B is placed in a perforated container; the container is placed in a 20-ml sample of commercial divinylbenzene containing 42.7% (wt) ethylvinylbenzene, 38.2% (wt) m-divinylbenzene and 19.1% (wt) p-divinylbenzene. The resin is allowed to remain in contact with the divinylbenzene mixture for 24 hours, after which the resin is transferred to a tube with a sintered glass plug, drained of free liquid, and washed with hexane followed by toluene. The results are shown below in Table III.

TABLE III

| Solvent | Volume (ml) | Weight (g) EVB | Weight (g) m-DVB | Weight (g) p-DVB | Component (%) EVB | Component (%) m-DVB | Component (%) p-DVB | Total Wt (g) |
| --- | --- | --- | --- | --- | --- | --- | --- | --- |
| Hexane | 9.5 | 0.434 | 0.367 | 0.163 | | | | |
| | 9.0 | 0.430 | 0.365 | 0.161 | 43.9 | 38.7 | 17.5 | 2.268 |
| | 10.0 | 0.131 | 0.145 | 0.072 | | | | |
| Toluene | 9.8 | 0.0431 | 0.160 | 0.102 | | | | |
| | 9.2 | 0.010 | 0.0395 | 0.0265 | 14.4 | 52.3 | 33.3 | 0.407 |
| | 10.2 | 0.0054 | 0.0132 | 0.007 | | | | |

EXAMPLE 4

This example repeated Example 3, except that the hexane wash is omitted. The results are shown below in Table IV.

TABLE IV

| Solvent | Volume (ml) | Weight (g) EVB | Weight (g) m-DVB | Weight (g) p-DVB | Component (%) EVB | Component (%) m-DVB | Component (%) p-DVB | Total Wt (g) |
| --- | --- | --- | --- | --- | --- | --- | --- | --- |
| Toluene | 9.3 | 0.956 | 0.922 | 0.440 | 41.2 | 39.8 | 19.0 | 2.318 |
| | 9.4 | 0.184 | 0.241 | 0.125 | 33.4 | 43.8 | 22.7 | 0.550 |
| | 9.1 | 0.299 | 0.066 | 0.037 | 74.3 | 16.4 | 9.3 | 0.403 |
| | 9.6 | 0.010 | 0.018 | 0.0105 | 25.8 | 46.9 | 27.3 | 0.038 |
| | 11.4 | 0.0036 | 0.008 | 0.0045 | 22.3 | 50.0 | 22.7 | 0.016 |
| | 9.8 | 0.0027 | 0.0041 | 0.0028 | 28.2 | 43.1 | 28.7 | 0.010 |

EXAMPLE 5

This example repeats Example 3, except that the resin is initially washed with methanol instead of hexane. The results are shown below in Table V.

TABLE V

| Solvent | Volume (ml) | Weight (g) EVB | Weight (g) m-DVB | Weight (g) p-DVB | Component (%) EVB | Component (%) m-DVB | Component (%) p-DVB | Total Wt (g) |
| --- | --- | --- | --- | --- | --- | --- | --- | --- |
| Methanol | 9.3 | 0.452 | 0.426 | 0.190 | | | | |
| | 9.4 | 0.349 | 0.337 | 0.150 | 41.7 | 40.3 | 18.0 | 2.193 |
| | 9.4 | 0.114 | 0.121 | 0.056 | | | | |
| Toluene | 9.5 | 0.071 | 0.151 | 0.094 | | | | |
| | 10.4 | 0.0174 | 0.046 | 0.031 | 21.6 | 48.1 | 30.2 | 0.447 |
| | 9.7 | 0.008 | 0.018 | 0.011 | | | | |

EXAMPLE 6

This example illustrates the separation of planar, chlorinated dibenzo molecules from the non-planar herbicide, 2,4,5-trichlorophenoxyacetic acid (2,4,5-T). In this example, radio-labeled 3,3′,5,5′-tetrachloroazobenzene is the planar impurity in the 2,4,5-T; its geometry, and hence its adsorbtive behavior, closely approaches that of the tetrachlorodioxins, but its toxicity is far lower.

A 5% methanol solution of 2,4,5-T was prepared, and to two 100 ml portions of this solution was added 3,3′,5,5′-tetrachloroazobenzene (TCAB) to produce a concentration of 0.5 ppm TCAB in each solution. To one of these solutions was added 5.000 g of Adsorbent A, and the resulting suspension and the "blank" without the adsorbent were both shaken on a mechanical shaker. The radioactivity of the solutions was determined after separating them from the adsorbents, at the times, and with the results, shown in Table IV below.

EXAMPLE 7

The procedure of Example 6 was repeated, except that Adsorbent B was used. The results are shown in Table VI below.

TABLE VI

| Contact Time | Blank (ppm TCAB) | Adsorbent B (ppm TCAB) | Adsorbent B (% removal) of TCAB | Adsorbent A ppm | Adsorbent A (% removal) of TCAB |
| --- | --- | --- | --- | --- | --- |
| 5 min | 0.431 | 0.304 | 29.5 | 0.423 | 1.9 |
| 24 | 0.426 | 0.0008 | 99.8 | 0.0024 | 99.4 |
| 48 hrs | 0.434 | 0.0003 | 99.9 | 0.0014 | 99.7 |

EXAMPLE 8

This example repeats the procedure of Example 7, except that smaller quantities of adsorbent were also used. The results of this example are shown in Table VII below.

TABLE VIII

| Adsorbent | Adsorbent Wt (g) | Final Conc (ppm) | Weight Adsorbed (μg) | Capacity (μg/g) |
| --- | --- | --- | --- | --- |
| Adsorbent B | 5.0 | 0.0003 | 42.2 | 8 |
| | 0.1 | 0.113 | 30.7 | 310 |
| | 0.01 | 0.355 | 6.7 | 670 |
| Blank | | 0.422 | | |

EXAMPLE 9

This example illustrates the removal of the polymerization inhibitor, hydroquinone methyl ester, from the monomer, methyl methacrylate. Such a process may be used to prepare acrylic monomers which polymerize more readily than inhibited monomers.

Columns were prepared by loading a methanol slurry of Adsorbent B (slurried overnight with methanol) until 50 ml of the adsorbent was transferred to the 1-cm-diameter, 50-cm-long chromatographic column. Excess methanol was drained off, leaving the adsorbent wet with methanol). Methyl methacrylate (MMA) containing hydroquinone methyl ester (MEHQ) was passed through the column at a rate of two bed volumes per hour, displacing the methanol. Two bed volumes (BV) of methyl methacrylate containing about 10 parts per million (ppm) hydroquinone methyl ester were passed through the column, followed by two bed volumes of methyl methacrylate containing about 50 parts per million hydroquinone methyl ester. Table VIII shows the results obtained using this procedure.

TABLE VIII

| MEHQ Concentration Influent MMA | MEHQ Concentration Effluent MMA | |
| --- | --- | --- |
| | 0.75–1.0 BV | 1.75–2.0 BV |
| 8.6 ppm | 0.3 ppm | 0.7 ppm |
| 49.4 ppm | 1.4 ppm | 3.3 ppm |

I claim:

1. A process for selectively removing planar molecules from a mixture containing planar and non-planar molecules which comprises contacting the mixture with a particulate adsorbent which is the product of controlled thermal degradation, at a temperature of about 500° C. or greater, of a macroporous synthetic polymer containing macropores ranging from about 50 to about 100,000 Angstroms in average critical dimension, and a carbon-fixing moiety, and derived from one or more ethylenically unsaturated monomers, or monomers which may be condensed to yield macroporous polymers, or mixtures thereof, until planar molecules have been selectively adsorbed, and subsequently separating the adsorbent from the mixture.

2. The process according to claim 1 wherein the particulate adsorbent is the product of controlled thermal degradation at from about 800° C. to about 1200° C.

3. The process according to claim 1 wherein the macroporous synthetic polymer is derived from a mixture of styrene and divinylbenzene.

4. The process according to claim 1 wherein the carbon-fixing moiety is sulfonate.

5. The process according to claim 4 wherein sulfuric acid is imbibed into the pores of the polymer prior to thermal degradation.

6. The process according to claim 1 wherein the planar molecules are divinylbenzene molecules and the mixture containing planar and non-planar molecules is a mixture of divinylbenzene and a minor amount of at least ethylvinylbenzene.

7. The process according to claim 6 wherein the adsorbed planar molecules are eluted from the adsorbent subsequent to its separation from the mixture.

8. The process according to claim 1 wherein the planar molecules are halogenated dibenzo-p-dioxin molecules and the mixture containing planar and non-planar molecules is a mixture of 2,4,5-trichlorophenoxyacetic acid or its water-soluble salts, and a minor amount of at least halogenated dibenzo-p-dioxin.

9. The process according to claim 1 wherein the planar molecules are inhibitors selected from the group consisting of quinone, hydroquinone, hydroquinone methyl ester, and mixtures thereof, and the mixture containing planar and non-planar molecules is an acrylic monomer inhibited with an inhibitor recited above.

10. The process according to claim 1 wherein the planar molecules are molecules of hydroquinone methyl ester and the mixture containing planar and non-planar molecules is methyl methacrylate inhibited with hydroquinone methyl ester.

* * * * *